United States Patent [19]

Reed, Jr.

[11] Patent Number: 4,877,618

[45] Date of Patent: Oct. 31, 1989

[54] TRANSDERMAL DRUG DELIVERY DEVICE

[76] Inventor: Fred D. Reed, Jr., Rte. 4, Box 855, Flagstaff, Ariz. 86001

[21] Appl. No.: 170,427

[22] Filed: Mar. 18, 1988

[51] Int. Cl.⁴ .............................................. A61K 9/68
[52] U.S. Cl. ................................ 424/448; 424/449; 424/486; 604/892.1
[58] Field of Search .......................... 424/422–425, 424/468–470, 473, 448, 449, 486; 604/892.1

[56] References Cited

U.S. PATENT DOCUMENTS

| | | | |
|---|---|---|---|
| 2,561,071 | 7/1951 | Prisk | 128/260 |
| 3,249,109 | 5/1966 | Maeth et al. | 128/268 |
| 3,598,122 | 4/1969 | Zaffaroni | 128/268 |
| 3,742,951 | 7/1973 | Zaffaroni | 128/268 |
| 3,797,494 | 10/1973 | Zaffaroni | 128/268 |
| 3,867,520 | 2/1974 | Mori | 424/36 |
| 3,936,573 | 2/1976 | Brockett | 428/402 |
| 4,008,719 | 2/1976 | Theeuwes | 128/260 |
| 4,014,334 | 2/1976 | Theeuwes | 128/260 |
| 4,058,122 | 12/1976 | Theeuwes | 128/260 |
| 4,060,084 | 1/1977 | Chandrasekaran | 128/260 |
| 4,077,407 | 3/1978 | Theeuwes | 128/260 |
| 4,144,317 | 9/1977 | Higuchi et al. | 424/21 |
| 4,225,460 | 9/1980 | Newell | 428/407 |
| 4,286,592 | 9/1981 | Chandrasekaran | 128/260 |
| 4,289,749 | 9/1981 | Keith | 424/28 |
| 4,291,015 | 9/1981 | Keith et al. | 424/28 |
| 4,314,557 | 2/1982 | Chandrasekaran | 128/260 |
| 4,321,117 | 3/1982 | Kaetsu et al. | 204/159 |
| 4,329,333 | 5/1982 | Barr | 424/19 |
| 4,344,929 | 8/1982 | Bonsen et al. | 424/15 |
| 4,432,964 | 2/1984 | Shell et al. | 424/14 |
| 4,434,153 | 2/1984 | Urguhart et al. | 424/22 |
| 4,452,775 | 6/1984 | Kent | 424/19 |
| 4,460,562 | 7/1984 | Keith et al. | 424/28 |
| 4,464,434 | 8/1984 | Davis | 428/402.22 |
| 4,475,916 | 10/1984 | Kimmelstein | 604/890 |
| 4,483,846 | 11/1984 | Koide et al. | 424/19 |
| 4,485,087 | 3/1982 | Otsuka et al. | 424/28 |
| 4,486,193 | 12/1984 | Shaw et al. | 604/897 |
| 4,490,322 | 12/1984 | Zierenberg | 264/205 |
| 4,493,869 | 1/1985 | Sweeny et al. | 428/905 |
| 4,525,340 | 4/1983 | Lange et al. | 424/16 |
| 4,524,095 | 10/1988 | Gockel et al. | 428/43 |
| 4,528,226 | 7/1985 | Sweeny | 428/905 |
| 4,687,481 | 8/1917 | Nuwayser | 424/449 |
| 4,710,191 | 12/1987 | Kwiatek et al. | 424/449 |

FOREIGN PATENT DOCUMENTS 0084817 5/1914 Japan .
0024811 5/1984 Japan .
8600806 2/1986 PCT Int'l Appl. .

OTHER PUBLICATIONS

"Transdermal Delivery of Drug", vol. I, Agis F. Kydenieus, Ph.D et al, CRC Press, Inc. (1987).
"Materials and Technology", vol. I, T. J. W. van Thoor, Debussy, Ellerman, Harms NV, Amersterdam (1968).

(List continued on next page.)

Primary Examiner—Ellis P. Robinson
Assistant Examiner—P. J. Ryan
Attorney, Agent, or Firm—Cahill, Sutton & Thomas

[57] ABSTRACT

A transdermal drug delivery device includes a plurality of adhesive laminae containing the drug to be transdermally administered which laminae are separated by alternating interlaminar layers within the device and extending in stacked configuration from a contact adhesive for adhering the device to the epidermis of a user. Modulated migration of molecules of the drug serially from and through the interlaminar layers to and through the contact adhesive results from the continous physical equilibration of the drug between the multiple alternating interlaminar layers and adhesive lamine which, when stacked, provide a relatively constant rate of dermal diffusion to the skin surface (dermis) for an extended period. Discharge of the drug other than through the contact adhesive is precluded by an impermeable backing layer. Side sealing may be necessary in some instances. The drug contained in this type of device may exist in either an equilibrated or constrained physical-chemical state.

44 Claims, 5 Drawing Sheets

OTHER PUBLICATIONS

"Studies of Nichotine's Effect on Brain Yield Ways to Kick Smoking Habit", David Stipp, *The Wall Street Journal*, p. 31, (Apr. 23, 1987).

"Transdermal Nicotine Reduces Cigarette Craving and Nicotine Preference", Jed E. Rose, Ph.D., et al., *Clinical Pharmacology and Therapeutics* 38(4), p. 450 (85), Transdermal Administration of Nicotine, *Drug and Alcohol Dependence*, 13, pp. 209–213 (1984).

"Dynamics Surface-Properties Due to Amine Migration and Chemical-Reaction in Primary Amilne Epoxide Systems"; R. T. Foister, *Journal of Colloid and Interface Science*, Vol. 99, No. 2, pp. 568–585, (1984).

"The Influence of Diffusion and Chemical-Reaction on Absorbtion Kinetics in Binary Surfactant Systems", R. T. Foister, Journal of Colloid and Interface Science, vol. 86, No. 2, pp. 386–410, (1983).

TRANSDERMAL DRUG DELIVERY DEVICE

CROSS-REFERENCE TO RELATED DISCLOSURE

Information relating to the invention described herein is contained in Disclosure Document No. 159164 filed on July 14, 1986 by the present inventor, which information is incorporated herein by reference.

BACKGROUND OF THE INVENTION

1. Field of the Invention

The present invention relates to drug delivery devices and, more particularly, to transdermal drug delivery devices (TDDD's).

2. Description of the Prior Art

Delivery of drugs transdermally has been in practice for some time and various devices have been developed for such purpose. Such known devices may be categorized as a reservoir device with a rate controlling membrane, a reservoir device without a rate controlling membrane, a monolithic system and a laminated structure. These devices are described in detail in Transdermal Delivery of Drugs, Volume I, pages 7-11, edited by Agis F. Kydonieus and Bret Berner, published by CRC Press, Inc., Boca Raton, Fla. Various patents have also been directed to transdermal drug delivery devices. In example, U.S. Pat. No. 4,286,592 is directed to a device having a reservoir for the drug to be administered. A contact adhesive layer in fluid communication with the reservoir serves in the manner of a conduit for transmission of the drug to an adhered skin surface. The adhesive layer equilibrates with the drug containing reservoir and determines the release rate for administration of the drug. Devices of this type generally provide a rapid initial administration followed by an asymptotically declining administration rate. For many drugs, such a varying rate of administration is unacceptable. In a monolithic type device the drug is disbursed throughout a carrier, layer or membrane in contact with the skin. In an adhesive dispersion type of device, the drug to be administered is disbursed throughout a layer of adhesive applied directly to the skin.

The delivery rate of the latter two types of devices identified above correspond closely with that of the reservoir type. That is, an initial rapid delivery rate exits which tapers, essentially asymptoically, over a period of time; the skin usually serves as the limiting factor of the absorption rate.

Transdermal drug delivery devices have been used for the delivery of scopolamine to counteract the nausea attenant sea sickness or motion sickness in land based vehicles. Generally, administration of this drug for a relatively short period of time and at an imprecise or unpredictable rate still seems to provide acceptable and beneficial results. For long term delivery of a specific drug, substantial control and regulation of the delivery rate may be of paramount importance.

Substantial literature exists to describe the difficulty with and low success rate of breaking the smoking habit. Some studies have concluded that the drug nicotine may be as or more addictive than most other habit forming drugs, such as heroin, cocaine, etc. Aside from the physical addiction that smokers may have, social and emotional dependencies attendant the manipulation of the smoking related implements and visualization of the smoke itself can constitute additional difficulties in breaking the smoking habit. Numerous experiments have been performed to explore the beneficial effects of transdermal delivery of nicotine as an adjunct to or in combination with a smoking cessation program. Although not conclusive, studies have indicated that transdermal administration of nicotine may be of assistance to a smoke participating in a smoking cessation program by segregating different aspects of the habit and thereby permitting therapeutic work on each such aspect.

Studies to date suggest that delivery of nicotine must extend commensurate with the normal smoking hours of a smoker. Furthermore, the delivery rate must be relatively commensurate with the depth of the smoker's habit. Without such near duplication of the level of nicotine to which the smoker has been accustomed, the craving for nicotine may be too overpowering to permit effective work on breaking the related aspects of the smoking habit. Irritant, mutagenic and carcinogenic hydrocarbon molecules, the secondary detriments attendant inhalation of smoke, which in fact may be more of a health hazard than nicotine, are not present during transdermal delivery of nicotine. Thus, a smoker has an immediate benefit if enabled to stop smoking even though the level of nicotine intake may remain essentially constant.

SUMMARY OF THE INVENTION

The present invention is direction to a transdermal drug delivery device for administering a drug at a relatively constant, but somewhat declining, rate for a substantial period of time. A plurality of stacked permeable adhesive laminae are permeated with the drug to be delivered. A plurality of particulate containing interlaminar layers onto which drug is adsorbed are alternately included between the adhesive laminae within the device. A covering of impermeable material on one end of the stack prevents dispersion of the drug through that end of the stack. A layer of contact adhesive on the other end of the stack secures the device to a user's skin. The layer of contact adhesive serves as a conduit for migration therethrough of the drug. If a contact adhesive is used which is different from the composite adhesive laminae the drug solubility should be lower in the contact adhesive than in the composite adhesive laminae. As the drug migrates through the contact adhesive layer to the skin, the adjacent interlaminar layer or adhesive lamina will experience a reduction in drug concentration. In an attempt to attain equilibration, based on relative drug capacities throughout the interlaminar layers and the adhesive laminae within the device, serial migration of the drug will occur through the stacked interlaminar layers and adhesive laminae to the contact adhesive layer. Such migration will result in an essentially constant, but somewhat declining, delivery rate of the drug from the contact adhesive layer to the adhered skin as the drug adsorbed in the interlaminar layers is depleted.

It is therefore a primary object of the present invention to provide a transdermal delivery device for delivering a drug at a slowly declining rate.

Another object of the present invention is to provide a transdermal drug delivery device for delivering a drug for a substantial period of time at a relatively uniformly declining rate.

Still another object of the present invention is to provide a transdermal drug delivery device havig a plurality of stacked drug permeated adhesive laminae interspersed with filled drug containing interlaminar layers.

Yet another object of the present invention is to provide a rupturable drug containing structure in a transdermal drug delivery device.

A further object of the present invention is to provide a pressure rupturable drug containing reservoir(s) within a transdermal drug delivery device.

A further object of the present invention is to provide a rupturable drug containing structure in combination with a stack of adhesive laminae interspersed with interlaminar layers in a transdermal drug delivery device.

A further object of the present invention is to provide multi-tiers of selectively rupturable drug containing structures in combination with a stack of adhesive laminae interspersed with interlaminar layers in a transdermal drug delivery device.

A further object of the present invention is to provide transdermal drug delivery device having a plurality of selectively rupturable drug containing structures in combination with a stack of drug permeated adhesive laminae interspersed with drug filed interlaminar layers.

A yet further object of the present invention is to provide a method for regulating transdermal delivery of a drug at a rate lower than the rate of absorption by the skin.

A still further object of the present invention is to provide a method for transdermally delivery a drug at a slowly declining rate for a substantial period of time.

A still further object of the present invention is to provide a method for selectively modifying an ongoing drug delivery rate of a transdermal drug delivery device.

A still further object of the present invention is to provide a method for selectively augmenting the ongoing drug delivery rate of a transdermal drug delivery device.

These and other objects of the present invention will become apparent to those skilled in the art as the description thereof proceeds.

BRIEF DESCRIPTION OF THE DRAWINGS

The present invention may be described with greater specificity and clarity with reference to the following drawings, in which.

DESCRIPTION OF THE PREFERRED EMBODIMENT

Figure 1:
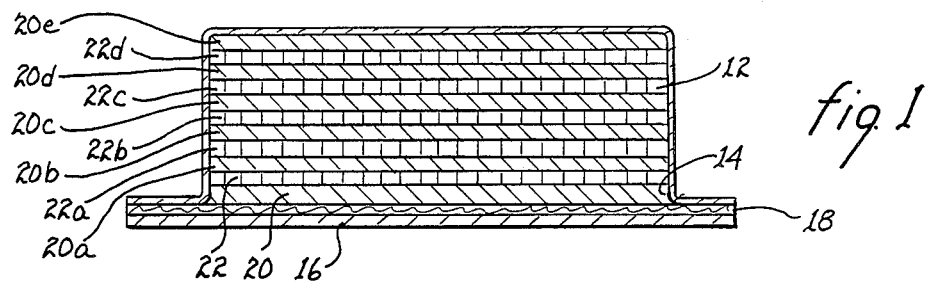
FIG. 1 is a representative cross sectional view of the components of the device.

Referring to FIG. 1, there is illustrated, in representative cross section, a transdermal drug delivery device 10. The device includes an impermeable cover 12 for housing the device system of the drug to be delivered. Typically, the cover may be a pigmented occlusive backing manufactured by the 3M Company such as item 3M Scotchpak 10005 or 10006. A port or opening 14 is defined by the cover through which the drug to be administered is discharged. The opening is initially sealed with a peelable liner 16, which liner is removed prior to use. The liner may be formed of kraft faced paper, such as that manufactured by Avery International, 3M Company and others or an occlusive liner, such as manufactured by the 3M Company, item No. MSX #437. Extending across opening 14 is a contact adhesive 18 for securing device 10 to the skin of a user. The adhesive may be of a type, such as, polyacrylic acidic adhesive (SP #18305) manufactured by Avery International, MSX #435 manufactured by 3M or silicone adhesive such as Dow Corning Bio PSA item No. X7-2960. This contact adhesive must be permeable to the drug to be delivered in order to permit migration of the drug through the adhesive to the adjacent skin. It is to be noted that cover 12 may be simply a backing with the sides of the device 10 being left uncovered. The loss of drug due to lateral outflow is essentially inconsequential because of the small surface area of the peripheral edge. However, the sides may be covered, depending on the drug application of the device.

The drug delivery and drug migration rate are primarily manifested by one or more pairs of adhesive lamina 20 and interlaminar layer 22. Each adhesive lamina 20 may be an adhesive permeated with the drug to be delivered. An adhesive suitable for this purpose, where the drug to be delivered is nicotine, is a polyacrylic acidic adhesive manufactured by Avery International and identified as item No. SP #18305. Interlaminar layer 22 serves the function of being a filled diffusion medium and may be formed, for example, by a layer of silica gel having particulate size in the range of 0.07 to 0.125 millimeters (mm.) (monoparticulate layer of Silica Gel G manufactured by Merck, Germany), or hydrous magnesium silicate (item number 24, 360-4 available from Aldrich Chemical Company of Milwaukee, Wis.) having a particulate size of approximately 0.01 mm. Depending upon the nature of the drug to be delivered, delivery rates and duration of delivery, a plurality of stages comprised of adhesive laminae and interlaminar layer pairings, 20,22 of variable natures or types may be stacked upon one another.

By inspection, it will be evident that in interlaminar layers 22 containing particulates the physical forms of the drug to be delivered will be the vapor or gaseous form permeating the interparticulate spaces, and in the particulate adsorbed form. For certain drugs, such as nicotine, the drug may migrate through interlaminar layer 22 and equilibrate or partition between adhesive laminae 20 primarily in a vapor state. If the drug is nicotine it should, also, adsorb well on interlaminar layers 22 if the layer is composed of a suitable adsorbent such as silicic acid or magnesium silicate. Within the adhesive lamina 20 and the contact adhesive laminae 18, the drug exists as a molecular dispersion.

Figure 2A:
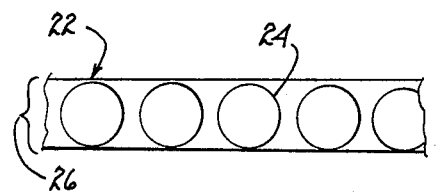
FIGS. 2a and 2b are partial cross sectional views of interlaminar layers.
Figure 2B:
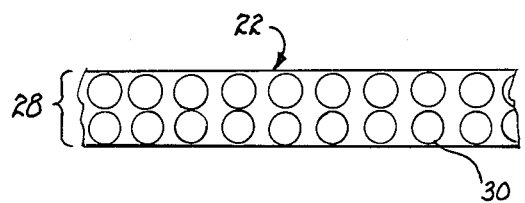

By inspection it can be seen that the drug capacity of an interlaminar layer 22 can be varied by changing the drug affinity or the surface area (since the drug adsorption process is primarily a surface phenomenon) of adsorbent material contained therin, thereby altering (increasing or decreasing) the "burst effect" interval release rate and/or duration and/or the duration of pseudo zero order drug release by the device depending on the area (distal or proximal) in which these changes are made. It should be noted that, in these variations, the drug vapor pressure and the drug vapor concentration, or partial pressure, in interlaminar layer 22 would remain essentially unchanged. However, the drug capacity of the interlaminar layer, that is, the amount of reserve drug adsorbed onto the surface of the particulates of the interlaminar layer, remains constant per unit area. A change in the particulate size of the adsorbent contained in the interlaminar layer does not change the drug capacity, assuming uniform spherical geometry, if particles 24 are present as a monolayer 26, as illustrated in FIG. 2a. Therefore, reducing the radius of the interlaminar particles 24 by half would allow inclusion of a particulate bilayer 28 in the area contained in the same volume, as represented by particulates 30 in FIG. 2b. This results in a two-fold increase in interlaminar layer surface area and drug storage capacity. Accordingly, increasing the drug capacity of the interlaminar layers 22 near contact adhesive 18 would result in an increase in intensity and/or duration of the "burst effect", or loading dose interval of the device due to a minimal resistance to diffusion to contact adhesive 18. That is, there are fewer adhesive laminae through which the drug must diffuse. Whereas, increasing the drug capacity of the interlaminar layers 22 near the occlusive backing or cover 12 would lead to a device exhibiting longer duration of pseudo zero order release function because of the increased resistance to drug diffusion to the contact adhesive and skin because more adhesive laminae 20 must be crossed en route to the contact adhesive/skin interface. Confirmation of these phenomena will be found in the discussion below attendant the graphs depicted in FIGS. 7a, 7b and FIGS. 8a, 8b.

Figure 3:
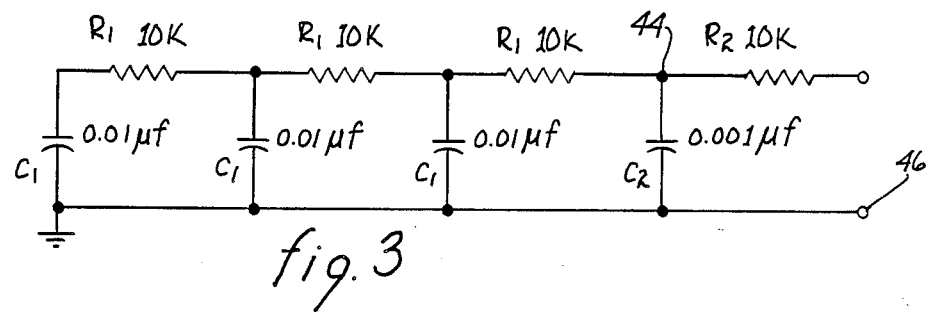
FIG. 3 is an analogous electrical circuit representing three stacked pairs of interlaminar layers and adhesive laminae plus a contact adhesive.
Figure 4:
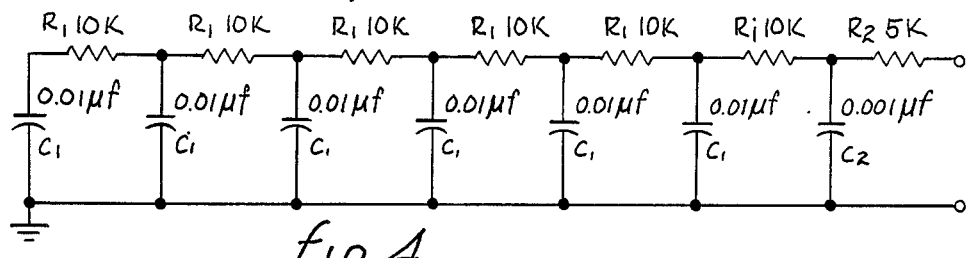
FIG. 4 is an analogous electrical circuit representing six stacked pairs of interlaminar layers and adhesive laminae plus a contact adhesive.
Figure 5:
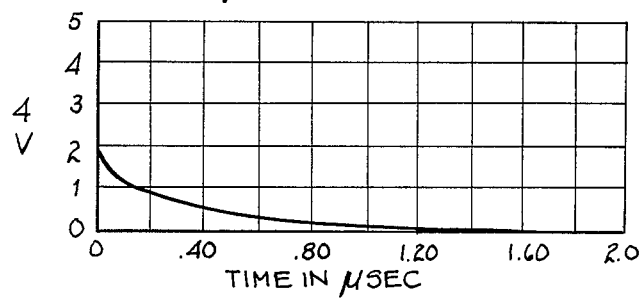
FIG. 5 is an output voltage curve repesentative of the analogous drug delivery rate simulated by the circuit shown in FIG. 3.
Figure 6:
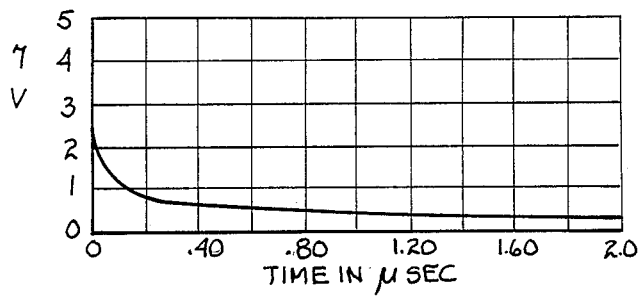
FIG. 6 is an output voltage curve representative of the drug delivery rate simulated by the circuit shown in FIG. 4.

In order to demonstrate the function of the transdermal drug delivery device in another physical system, a model electrical circuit has been constructed using a circuit simulation computer program. (Micro Cap II, Spectrum Software, Sunnyvale, CA). FIGS. 3 and 4 are schematic diagrams representing 3 stage and 6 stage electrical circuits, 40, 42. The capacitors $C_1$ and the resistors $R_1$ in these circuits represent the drug vapor pressure in the interparticulate spaces of the interlaminar layers and the diffusional resistance of the adhesive laminae of the multilaminated transdermnal drug delivery device, respectively. Capacitors $C_2$ and resistors $R_2$ represent the drug concentration in the contact adhesive and the resistance to drug molecules leaving the device or in reaching the skin surface, respectively, and approximate the "burst effect". The voltage across nodes 44, 46 represents the drug delivery rate to the skin. FIGS. 5 and 6 show the relative system discharge curves (voltage vs. time-micro seconds) for the circuits shown in FIGS. 3 and 4, rsepectively. These data demonstrate that a two-fold increase in the number of capacitors and resistors in this type of circuit results: (1) in an increase in the discharge interval; and, (2) a correspondingly more linear, pseudo zero order, discharge curve. There is no increase in the initial discharge interval or the voltage, which corresponds to the "burst effect" interval and the rate of drug release, respectively, in the multi-laminated, stratified dispersion field drug delivery devices.

These electrical circuit simulations demonstrate the contribution of each stage to the total flux of the device. They are not capable of demonstrating the relative maintenance of drug vapor pressure in the physical systems of these transdermal delivery devices provided by the equilibrating effects of the release of adsorbed drug into the interlaminar layer, interparticulate spaces. They serve as reasonable models for demonstrating the duration of function and the release kinetic profiles of the initial release phases which can be expected from such devices as these.

The time values of the electrical models and the physical TDDD's differ markedly because of equilibration differences in the example systems. The electrical models exhibit near instantaneous equilibration whereas the physical TDDD's equilibrate more slowly because the desorption of drug molecules adsorbed on the particles in the interlaminar layer is slow and a high degree of drug solubility in the adhesive laminae also seems to slow device equilibration.

The major advantage of the stratified diffusion field lies in a high degree of flexibility in drug flux. That is, the drug storage areas need not be uniformly distributed as is the case in other diffusion field devices. For instance, if a larger "burst effect" intensity or loading dose interval is required, more drug storage capacity could be included in the frontal or proximal interlaminar layers nearer the contact adhesive. Conversely, but not mutually exclusively, if a very long duration of release is desired more drug storage capacity could be included in the deeper interlaminar layers, nearer the occlusive backing layer of the device.

Figure 7A:
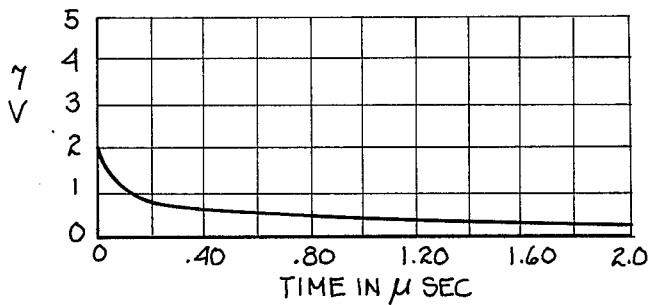
FIGS. 7a and 7b are voltage discharge curves generated by a distally loaded variant of the circuit shown in FIG. 4, FIG. 7a describes the discharge rate of the entire circuit, while FIG. 7b describes the discharge rate of the stage 6, most distal, capacitor.
Figure 7B:
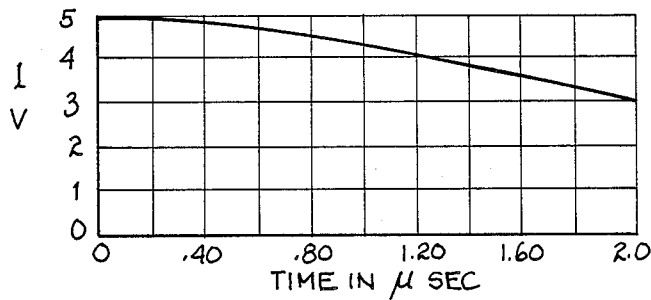
Figure 8A:
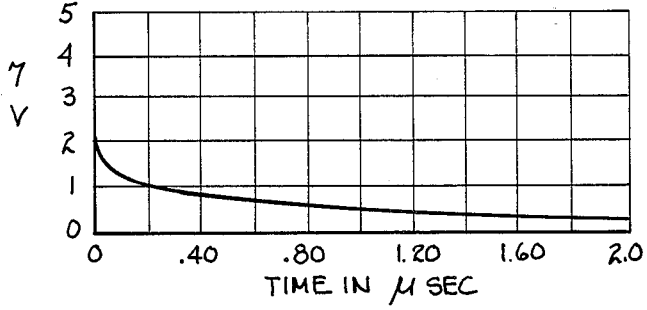
FIGS. 8a and 8b are voltage discharge curves generated by a proximally loaded variant of the circuit shown in FIG. 4, FIG. 8a describes the discharge rate of the entire circuit, while FIG. 8b describes the discharge rate of the stage 6, most distal, capacitor.
Figure 8B:
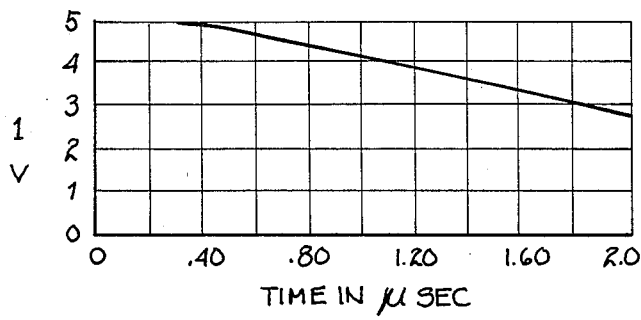

These phenomena are shown in FIGS. 7a, 7b and 8a, 8b. FIGS. 7a and 7b illustrate the alteration in discharge rate of a six (6) stage electrical system exhibiting increased distal capacitance (corresponding to increased drug storage capacity near the backing layer or most distant from the skin). To generate the graph shown in each of FIGS. 7a and 7b, the capacitance of capacitor $C_1$ in the fifth and sixth stages (simulative of the distal interlaminar layers, i.e. farthest, from the skin attachment site) was doubled to 0.02 microfarad. The graph in FIG. 7a shows the circuit discharge rate corresponding to drug release at the skin attachment site and the graph in FIG. 7b shows the discharge rate of capacitor C, corresponding to the concentration in the distal interlaminar layer of the drug to be administered. FIGS. 8a and 8b illustrate the alteration in discharge of a six (6)

stage electrical system exhibiting increased proximal capacitance (corresponding to increased drug storage capacity near the skin or contact adhesive). To generate the graph shown in each of FIGS. 8a and 8b, the capacitance of capacitor $C_1$ in the first and second stages (simulative of the proximal interlaminar layers, i.e. closest, to the skin attachment site) was doubled to 0.02 microfarad. The graph in FIG. 8a represents the circuit discharge rate simulating drug release at the skin attachment site and the graph in FIG. 8b represents the rate of discharge of the sixth stage capacitor, simulating the decay rate of the drug concentration at the distal interlaminar layer. It should be noted that the discharge curves of FIGS. 7a and 8a cross at approximately 2 microseconds. However, the proximally loaded system exhibits a steeper sloped curve or higher rate of discharge which would be manifested in a TDDD as a larger "burst effect" or "loading dose". The distally loaded system would more closely conform to the release rate of the TDDD in Experiment B of device 10 in which more proximal resistance was incorporated into the device. The stratified diffusional field TDDD, therefore, provides for incorporation of drug or drug capacity in regions both proximal and distal (i.e. at large and small distances from the skin) in which the drug molecules are presented with either less or more diffusional resistance during migration toward the skin, respectively.

Figure 9:
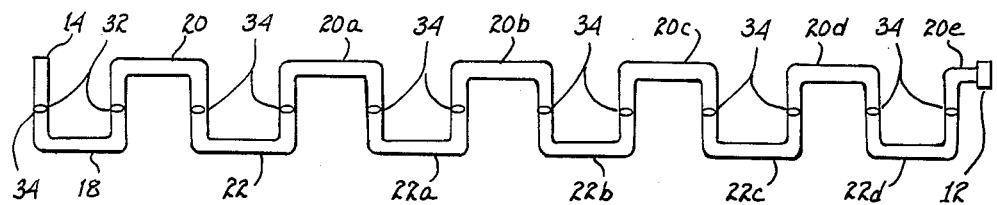
FIG. 9 is a functional representation of the present invention.

Referring to FIG. 9, there is illustrated a functional representation of the operation of device 10. In particular, five and a half pairs of stacked interlaminar layers and adhesive lamina are illustrated and referenced by numerals 20, 22, 20a, 22a, 20b, 22b, 20c, 22c, 20d, 22d and 20e as extending between cover 12 and contact adhesive 18 in juxtaposed relationship with opening 14. Element 32 represents the resistance encountered by the drug delivery at the skin. functionally, device 10 may be represented, as illustrated, as a serpentine like conduit wherein the upper half of each convolution contains the drug to be administered dispersed in adhesive laminae 40 and the lower half of each convolution contains the drug to be administered in gaseous form and/or reversibly adsorbed onto the particular material in the interlaminar layers. An interface 34 exists at each point of transition between the two composite phases of the drug to be delivered.

Figure 10:
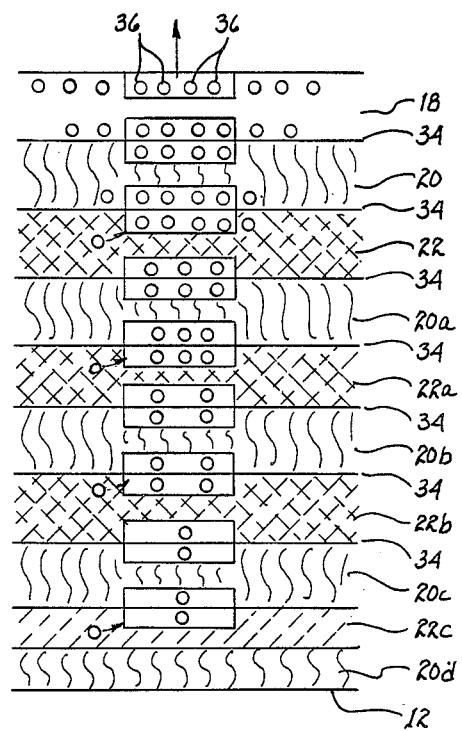
FIG. 10 illustrates the migration through the device of drug molecules of the drug to be delivered.

Referring jointly to FIGS. 1, 9 and 10, migration of the drug to be delivered through device 10 will be described. Prior to removal of release liner 16, extending across the contact adhesive layer 18 to expose the interior of the device 10, the drug will be partitioned between the composite adhesive laminae and the composite interlaminar layers and the contact adhesive. Upon removal of the release liner, a burst of drug release will ensue. This is apparently caused by drug molecule migration to and accumulation at the contact adhesive lamina 18/release liner 16 interface and the equilibration with air and the inside surface of the packaging envelope during storage. After this first order or "burst" drug release burst phase subsides, the concentration of the drug in contact adhesive lamina 18 (opening 14 in FIGS. 1 and 7) will decline to a concentration less than the drug concentration in the underlying adhesive laminae 20. This drug vapor pressure or drug concentration imbalance is compensated by underlying adhesive laminae 20 and underlying interlaminar layers 22, such that, as the outflow of drug molecules to the skin depletes contact adhesive 18, partitioning effects will result in maintenance of approximately the required drug concentration in the contact adhesive from either the underlying adhesive lamina 20 (or from an underlying interlaminar layer 22) which then serially equilibrates with the next underlying interlaminar layer 22 (or the next underlying adhesive lamina 20). Interlaminar layer 22 then equilibrates with adhesive lamina 20a; adhesive lamina 20a then equilibrates with interlaminar layer 22a. The reduced drug concentrations in the adhesive lamina will produce a modulated equalizing flow of drug molecules through adhesive lamina 20, 20a, 20b, 20c, 20d and 20e though respective interfaces 34 with interlaminar layers 22, 22a, 22b, 22c and 22d. This allows maintenance of the same number of drug molecules in all of the adhesive laminae, while withdrawing the drug molecules which have been adsorbed in the interlaminar layers. The device then functions as a "modulated, stratified equilibrium drug reservoir" or, more specifically, a stratified diffusional field.

The adhesive laminae offer reistance to drug diffusion and, thereby function (in Equation 2) as resistors in a serial diffusional field similarly as resistors in a serially connected electrical circuit (in Equation 1):

$$\text{Equation 1: } i = \frac{E}{R}$$

$i$ = current
$E$ = potential (difference)
$R$ = resistance to electrical conductance $$\text{Equation 2: } F = \frac{\Delta C}{R}$$

$F$ = drug flux or the amount of drug released per unit of time
$\Delta C$ = difference in concentration across an adhesive laminae
$R$ = resistance to diffusion (drug) through the adhesive laminae Beginning at the backing layer 12 and proceeding toward the contact adhesive 18 the resistance for each stage is reduced by the value of one adhesive lamina 20.

$$F_1 = \frac{\Delta C}{\Sigma R}$$

$F_1$ = Component of device flux contributed by the deepest interlaminar layer $$F_2 = \frac{\Delta C}{(\Sigma R) - R}$$

$F_2$ = Component of device flux contributed by the next to deepest interlaminar layer As particularly illustrated in FIG. 8, if four molecules 36 of the drug depart from adhesive lamina 20 via contact adhesive layer 18, the four molecules will be replenished by the four underlying interlaminar layers by drug desorption i.e. release of drug molecules adsorbed on the particulate material contained therein. Four molecules will be released from the interlaminar layer 22 via the adhesive lamina 20a. The resulting imbalance between interlaminar layer 22 and 22a will result in a flow through lamina 20b . . . etc. to adhesive lamina 20a. The net result is that each of interlaminar layers 22, 22a, 22b and 22c contributes one molecule 36 of the four molecules discharged from contact adhesive 18. This then functions as a stratified diffusional field. In summary, the interlaminar layers contain the drug capacity in the form of particulate surface adsorbed drug. This adsorbed drug is in equilibrium with the drug present in the interlaminar layer open spaces in the vapor phase. The drug which is in the vapor phase is in equilibrium with the drug dispersed in the adhesive laminae.

Such continuing modulated replenishment of downstream adhesive laminae from upstream adhesive laminae due to the drug concentration differences in the interlaminar layers will result in a close to uniform rate of discharge by device 10. Necessarily, because there is a continuing depletion of the drug from within device 10, the flow rate will decline over a period of time as adsorbed drug in the interlaminar layers becomes insufficient to maintain the requisite concentrations in the adhesive laminae. Nevertheless, except for an initial burst of drug delivery due to the sudden substantial imbalance in drug concentration between the skin and contact adhesive layer 18, the rate of decline of discharge is essentially constant. Furthermore, the discharge rate is also a function of the drug absorption characteristics or capacity of the skin to which device 10 is attached. Although device 10 is designed to function more or less as described, alterations or changes in the physical or chemical natures of the adhesive laminae, the contact adhesive and/or the interlaminar layer materials could yield a device in which the interlaminar layers dominate the function of resistance to diffusion and the adhesive laminae dominate as drug storage modules.

The present invention was developed primarily as a vehicle for dispensing nicotine to aid a user during participation in a smoking cessation program. Accordingly, a number of experiments have been conducted wherein the drug to be delivered was nicotine.

Figure 11:
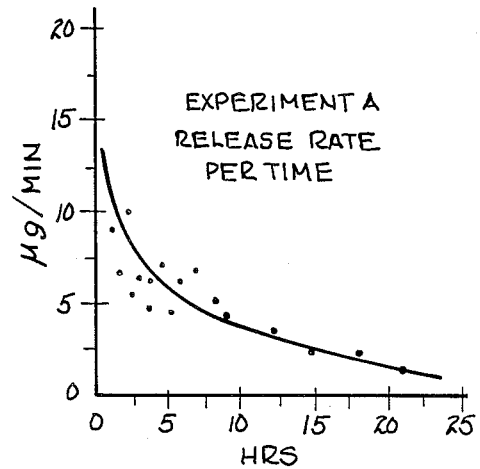
FIGS. 11, 12 and 13 illustrate graphs representative of drug delivery rates under certain circumstances.

For Experiment A device 10 was constructed as follows. A 4 percent (4%) dispersion of 3M acrylic acidic adhesive, MSX#435 in heptane was coated onto a 0.033 mm thick layer of the same adhesive developed on the release liner which resulted in a 0.075 millimeter thick layer of adhesive. This adhesive lamina was applied to a 0.07 millimeter thick occlusive pigmented backing of (3M Company, Scotchpak No. 10005 or 10006). Nicotine (2.81 milligrams) was applied in a (6 milligram per milliliter) hexane solution to a ten square centimeter section of the backing applied adhesive. After drying, a particulate monolayer of hydrous magnesium silicate (to a thickness of 0.01 millimeters) was applied to the adhesive lamina (having nicotine uniformly incorporated or dissolved therein) to serve as a separating layer wherein a concentration of nicotine would exist proportional to the relative capacities of the other components of the device. A total of four alternate adhesive laminae and interlaminar layers were applied to the backing. An acrylic acidic contact adhesive lamina (of a thickness of 0.033 millimeters) was applied to the last separating layer. Thereafter, a silanized release liner was applied and left in place. After a three hour equilibration time, the release liner was removed and the rate of nicotine release was determined by standard procedures. A graph of the release rate is depicted in FIG. 11. Such a release rate may be useful for administering nicotine for approximately 24 hours to produce systemic blood levels of nicotine which approximate those of a tobacco smoker. A device constructed in accordance with Experiment A could be of great value in assisting smokers in a smoking cessation program.

Figure 12:
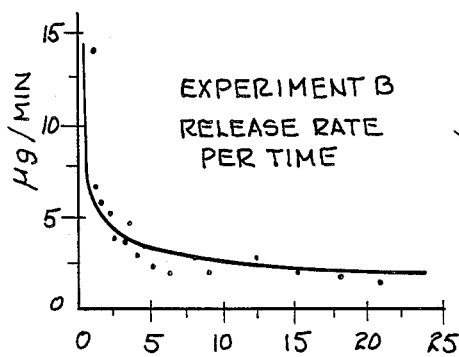

In Experiment B, a device 10 was prepared as follows. Acrylic acidic adhesive (to a thickness of 0.033 millimeters) was applied to a 0.07 millimeter thick occlusive pigmented backing (3M Company, Scotchpak No. 10005 or 10006). Nicotine (1.38 milligrams) in a hexane solution (6 milligramns per milliliter) was applied to a ten square centimeter section of the backing applied adhesive. After drying, a particulate monolayer of hydrous magnesium silicate (to a thickness of 0.01 millimeters) was applied to the adhesive lamina to serve as a separating layer. An alternate procedure, other than incorporating nicotine into the adhesive formulation, is that of applying the magnesium silicate to the adhesive lamina and spraying a nicotine solution onto the magnesium silicate layer or mixing the nicotine with the magnesium silicate before application to the adhesive lamina or providing a "well" source or reservoir of nicotine at the backing layer. Furthermore, a "well" could be incorporated, which "well" could contain pure drug, a drug solution or a friable microencapsulated drug containing structure which structure can be crushed to initiate drug equilibration within the TDDD. A total of six (6) adhesive laminae and interlaminar layers were alternately applied. The last magnesium silicate layer was covered with a lamina of acrylic acidic adhesive to a thickness of 0.033 millimeters and covered with a silicone contact adhesive (such as Bio PSA×7-2960, Dow Corning) to a thickness of 0.3 millimeters to secure a release liner (such as 3M Scotchpak No. 1022). The silicon adhesive exhibits different nicotine solubility and/or a different diffusion rate that the composite adhesive lamina 20. After three hours, the release liner was removed and the rate of nicotine release was determined by standard procedures. FIG. 12 depicts a graph representing the nicotine release rate.

In conclusion, the device built in accordance with Experiment A provides a relatively steady release rate after approximately a 14 hours release interval whereas the device built in accordance with Experiment B provides a steady release rate (pseudo zero order kinetics) beginning at approximately 4 hours. The stratified diffusional device 10 is particularly easily modified to include structural components capable of delaying equilibration between the adhesive laminae and the interlaminar layers of the device, thereby, delaying drug release from the device.

A TDDD having a drug "well" of an encapsulating structure which is friable or pressure rupturable and contains a drug behind or within the friable or pressure rupturable structure until the time of use has the advantages of extended shelf life and decrease in or removal of "burst effect" possibility so long as the friable structure is intact. The only possible disadvantage is that a lag time for drug release to the skin would exist, which would require that the user disrupt the friable structure constraining the drug, perhaps, a number of hours prior to the required drug use (i.e. The user could disrupt the friable structure and apply the device prior to retiring in the evening). Alternatively, additional drug could be incorporated into the more proximal stages of the device in order to provide initial drug release at the desired rate. Whereas, the stratified field transdermal drug delivery device is particularly well suited to inclusion of such encapsulated drug structures, the drug encapsulation and concomitant drug equilibration delay feature could be used to markedly increase storage life and decrease "burst effect", where problematic, in other transdermal drug delivery device designs.

The structure of such a "well" to be used with a TDDD could incorporate the following components: (1) polyethylene backing layer; (2) polyacrylic acidic adhesive lamina (3M or Avery); (3) perforated polyethylene layer serving as the "well" structure (X is excised); (4) magnesium silicate particulate monolayer applied only inside the X of the well structure; (5) drug applied to the magnesium silicate; (6) polyacrylic acidic adhesive lamina (3M or Avery); and (7) glass cover slip (Corning glass), plastic cover slip, silicate cement layer, fused salt or other rupturable layer to serve as friable structure; a mixture of sodium silicate with any of several materials (as discussed further in Materials and Technology, Volume I, edited by T. J. W. van Thoor and Published in 1968 by DeBussy, Ellerman, Harmus NV, Amsterdam) may be used as the friable structure. The rest of the TDDD (constructed as noted above) is then applied to the glass cover (starting with an adhesive lamina). Modifications of this principle are obvious. Alternatively, the drug "well" or reservoir contains rupturable drug containing microcapsules, such as described in U.S. Pat. Nos. 4,528,226, 4,493,869 and 4,225,460, which are physically disrupted prior to use could be used. Likewise, additional drug incorporated in the proximal stages of device 10 allows drug phasing and/or peaking of drug delivery. This feature also allows the incorporation of physicochemically incompatible drugs in a single device.

Figure 14:
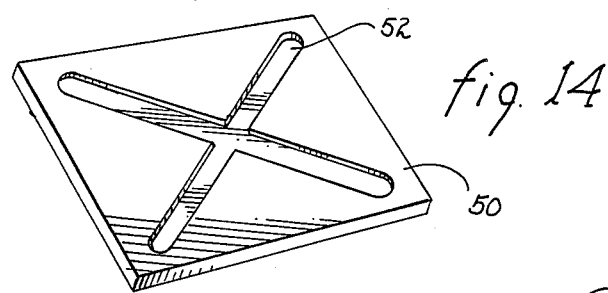
FIGS. 14, 15 and 16 illustrate a variant of the device wherein a "well" or pressure rupturable encapsulating structure is employed to serve as a source for the drug to be administered.
Figure 15:
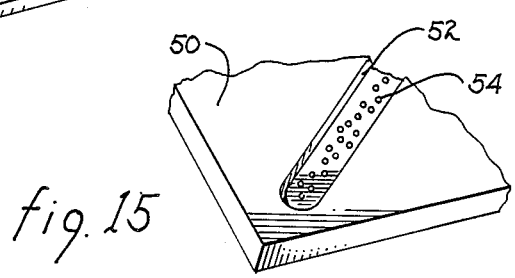
Figure 16:
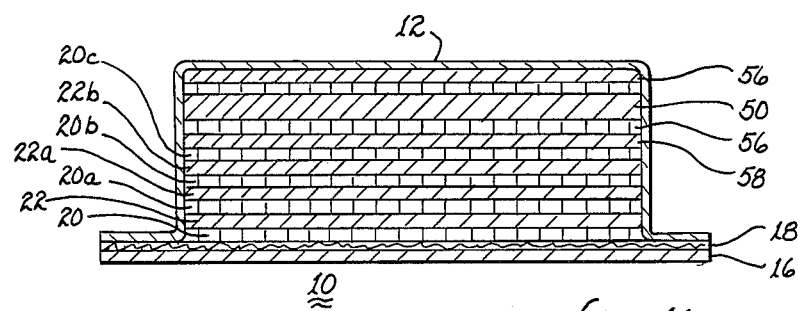

The structure and operation of an embodiment of a TDDD described above will be elaborated upon in reference to FIGS. 14 through 16. FIG. 14 illustrates a perforated layer 50, which may be of polyethylene, that serves as a "well" for the drug to be administered. The "well"(s) itself is defined by the perforation(s) formed within the layer. As illustrated in FIG. 14, one such configuration of a perforation 52 may be an X. The drug to be administered is deposited within the X and retained therein by sheets of material on opposed sides of layer 50, the proximal sheet being of a rupturable nature. The sheets may or may not be held in place by adhesive or, alternatively, by sealing the peripheral edge of the device or internal "well" edge sealing. The form of the drug disposed within the perforation may be a drug impregnated magnesium silcate particulate monolayer; alternatively, the drug may be encapsulated within a multitude of friable or rupturable microcapsules 54, as represented in FIG. 15. The quantity of drug within layer 50 is, of course, a function of the depth or thickness of the layer and the platform of the perforation therein.

Referring to FIG. 16 there shown a variant of device 10 having a drug "well" added thereto. Layer 50 is secured to cover 12 through adhesive lamina 56. After such attachment of the layer, the perforation therein may be filled with a drug absorbing substance such as a magnesium silicate particulate monolayer which has been impregnated with the drug to be delivered; alternatively, microcapsules 54 may be disposed within the perforation. A further adhesive lamina 56 is applied to the other side of layer 50. A friable or rupturable glass cover 58 is secured to layer 50 through the adhering action of adhesive lamina 56. The glass cover prevents or precludes migration of the drug to be administered from layer 50 until such time as the glass cover is ruptured. Thereafter, the drug migrates laterally along the glass cover and through the openings provided by the fracture lines in the glass cover. Adjacent the glass cover are two or more pairs of adhesive lamina 20 and interlaminer layers 22 terminating in an adhesive lamina 20. Under certain circumstances a single adhesive lamina adjacent the rupturable structure may be sufficient to provide a sealable or advantaged device. A contact adhesive 18 is disposed adjacent the last adhesive lamina 20 and the flange portion of cover 12 to assist in maintaining device 10 attached to a user's skin. A liner 16 is attached to contact adhesive 18 to seal device 10 prior to use; liner 16 is removed for application of the device to the skin of a user.

After attachment of device 10, a force is applied to the device to rupture glass cover 58. Thereafter, by molecular migration the drug will migrate through the adhesive lamina, the interlaminer layers and contact adhesive 18 and into the underlying skin.

The configuration illustrated in FIG. 16 provides a wide latitude of modes of operation. In example, each of adhesive lamina 20 may be impregnated with the drug to be administered (as described previously in reference to FIG. 1) to provide a migration of drug molecules to the skin after attachment of the device. After a time interval, the encapsulating structure(s) or, glass cover 56 may be ruptured to provide a further source of drug to be administered. Or, the glass cover may be ruptured upon application of variant 10 to provide migration of drug to the skin from both the plurality of adhesive lamina and the "well" formed in layer 50. In yet another embodiment, glass cover 58 may be ruptured at some point in time prior to use to permit the deivce to equilibrate prior to use. It is contemplated that in certain other variants, the number of pairs of adhesive lamina 20 and interlaminer layers 22 may be increased or decreased from the three pairs illustrated in FIG. 16. Necessarily, if occlusive microcapsules 54, that is, do not release drug during storage, are employed in layer 50, the need for glass or other cover is vacated. In the latter case, to obtain migration of the drug encapsulated within the microcapsules, sufficient pressure would be applied to the perforation within layer 50 to rupture the microcapsules and thereby obtain release of the encapsulated drug and permit commencement of migration of the drug.

Figure 17:
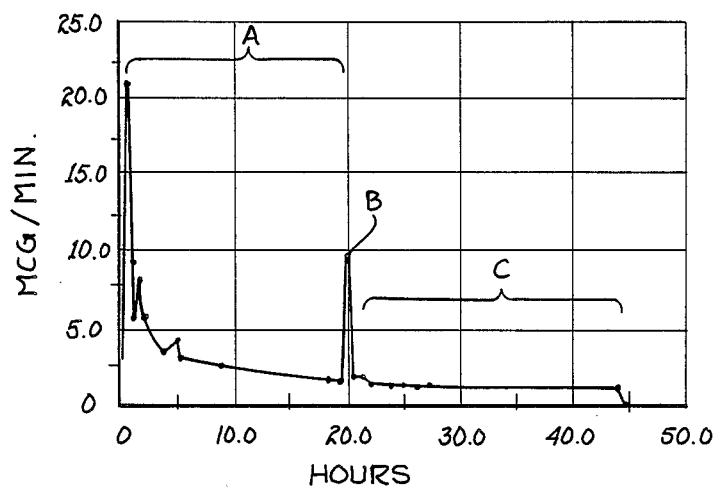
FIG. 17 illustrates a graph of the drug delivery rate pertinent to a device of the type illustrated in FIG. 16.

Referring to FIG. 17, there is illustrated a graph of the micrograms of nicotine released per minute from a variant of the structure illustrated in FIG. 16. In this variant, glass cover 58 was of a size approximately 50 percent of the area of layer 50. Accordingly, migration of the drug from within the perforation of layer 50 had to flow laterally to the edges of the glass cover and therefrom begin a migration through the adhesive lamina and interlaminer layers. These test devices were allowed to so equilibrate at 25° C. for 40 days. The drug release rate for the initial 20 hours is reflected by portion A of the graph. At the end of 20 hours, the partial glass cover was ruptured. Such rupture eliminated the need for the drug to flow laterally along the glass cover and it could flow through the fractures developed therein. Such removal of impediment to flow produced a "burst" of drug release (identified by the letter B) of the drug. Thereafter, during the portion of the graph identified by letter C, the release rate was essentially constant, rather than essentially constantly tapering as illustrated in the right hand side of portion A.

Figure 18:
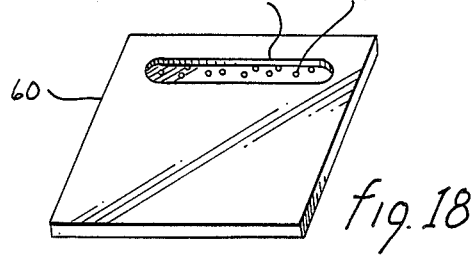
FIGS. 18, 19 and 20 illustrate configurations of layers serving as stacked "wells" in a further variant.
Figure 19:
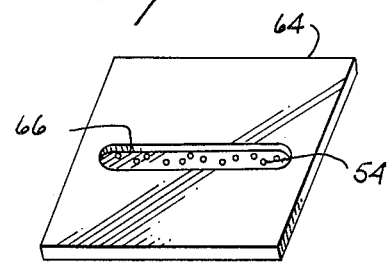
Figure 20:
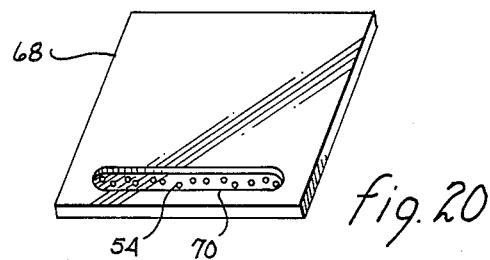

Referring to FIGS. 18, 19 and 20, there are shown three layers 60, 64 and 68 which include non-overlapping perforations 62, 66 and 70, respectively. Each of these perforations ("wells") may be filled with microcapsules 54 containing an encapsulated drug, a magnesium silicate particulate layer impregnated with the drug to be administered or other drug permeated medium from which the drug may be dispensed on command. That is, the "wells" are for receiving drug encapsulated structures or for becoming drug encapsulating structures.

Figure 21:
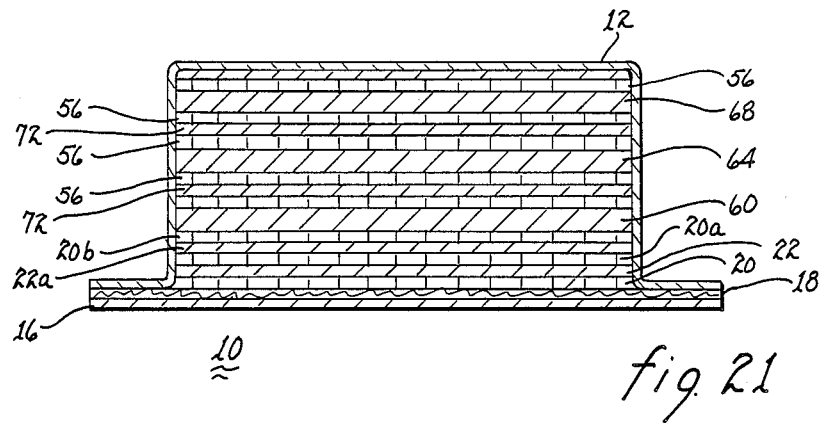
FIG. 21 is a cross sectional view of the further variant of the device.

By stacking layers 60, 64 and 66, as illustrated in FIG. 21, three independent "wells" may be developed in a yet further variant of device 10. In example, intermediate layer 60 and layer 64, there may be disposed a friable or rupturable or pressure rupturable cover 72 to prevent migration of the drug between these two layers. A further cover 72 may be disposed intermediate layer 64 and layer 66 to prevent drug migration therebetween. To prevent diffusion of the drug around the edge(s) of the cover, the latter must cover the entire "well"; other methods and structure may also be incorporated to prevent any unwanted diffusion of the drug around the edge(s) of the cover. It is understood that the forward or proximal "well" cover must be ruptured first in the function activation sequence. Thereafter, the second and subsequent covers over the more distal "wells" are ruptured in conformance with the drug administration sequence. To ensure accurate and specific sequential ruptures of the covers, each fused salt or silicate cement restraining cover may be sized and positioned to be used only with and directly over each "well" perforation; by locating the "well" perforations in a non-overlapping arrangement within a stack, discrete rupturing of any specific cover can be achieved.

Upon application of device 10, by removal of liner 16 to adhere the device through contact adhesive 18 to the skin of a user, migration of the drug will flow through interlaminar layers 22, adhesive lamina 20 may or may not be drug impregnated. At some later time, encapsulating structure (s) 54 contained in the perforation (s) of layer 60 or cover 72 proximal to layer 60 may be fractured by applying pressure to the corresponding area of cover 12. Such fracturing will permit migration of drug from within perforation 62 downwardly through the pairs of adhesive laminae (20) and interlaminar layers (20, 22), through the contact adhesive layer where the drug is released to the skin. At some later time, the next most proximal layer 64 containing restrained drug molecules by either encapsulating structures 64 or cover 72 in perforation 66 may be fractured by pressing on the area of cover 12 corresponding to perforation 66. Such fracturing will permit migration of the drug from perforations 66 through perforation 62 of layer 60, downwardly through the adhesive laminae and interlaminar layers to the contact adhesive where the drug is released to the skin. At still some later point in time, the next proximal layer 68 (most distal in FIG. 21) containing restrained drug molecules by either encapsulating structures 54 or cover 72 in perforation 70 may be fractured by pressing on the area of cover 12 corresponding to the area of perforation 70. Such fracturing will permit migration of the drug downwardly from perforation 70 of layer 68, through perforation 62 of layer 60, through the adhesive laminae and interlaminar layers to the contact adhesive where the drug is released to the skin. It will ultimately migrate through the stack illustrated in FIG. 21. It will be appreciated that layers 60 and 64 may include further non-drug containing perforations in alignment with the drug containing perforations of the adjacent layer to avoid the necessity for lateral migration along the surface of the layers in order to reach an aperture and penetrate the layer and in such case would permit fracturing of the restraining structures of the drug containing perforations in any layer sequence; i.e. distal first instead of last. Alternatively, multiple separate perforations, "wells" could be included in a single layer.. Furthermore, the number, configuration and orientation of the perforations in the plurality of drug "well" layers may be modified to meet particular needs, user requirements or satisfy other criteria attendant the administration of any particular drug.

A study reported in an article entitled "Transdermal Nicotine Reduces Cigarette Craving and Nicotine Preference", published in *Clinical Pharmacology and Therapeutics,* Vol. 38 (4) pages 450 to 456, (1985) indicates that a sustained nicotine discharge level over an extended period of time should improve compliance with a smoking cessation program. As evidenced by test conducted with the present invention, device 10 is capable of sustaining a sufficient rate of delivery of nicotine for a 24 hour period. It may therefore be assumed that device 10 may be of incalculable value to a smoker having difficulty in complying with a smoking cessation program.

Figure 13:
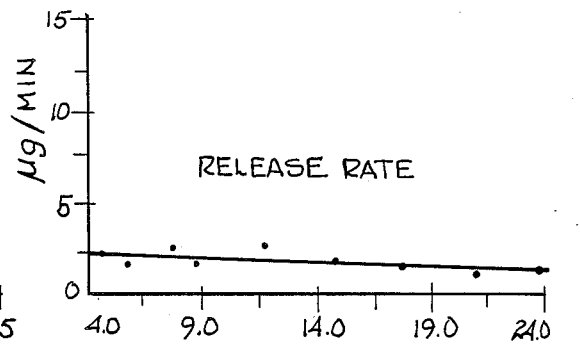

A further test published in 1984 "Transdermal Administration of Nicotine", *Drug and Alcohol Dependence,* Vol. 13, pages 209, 213 (1984) and describing application of 9 mg of nicotine in a 30% aqueous solution to the underside of the left forearm and covered by a thin layer of polyethylene for delivery transdermally of nicotine indicates that an increase in salivary nicotine was maintained for aproximately four hours. Thereafter, an approximately steady state essentially equivalent to the results of initial testing prior to administration was maintained for a twelve hour period. With the present invention, such initial rapid nicotine level and subsequent rapid decline resulting from use of such a reservoir type transdermal device, as described above, would not occur. Using a previously equilibrated stratified diffusion device instead, after an initial burst of nicotine delivery, a relatively slowly declining rate of delivery would be sustained at an elevated level for at least up to 24 hours, as depicted in FIG. 13. Alternatively, use of a non-equilibrated type of encapsulated drug device would delay the release of drug to the skin for a time interval during which drug is equilibrating within the device after rupture of the drug encapsulating structure(s).

The 1984 study also indicated several potential advantages for using a device 10 as part of a smoking cessation treatment. These include elimination of the side effects attendant nicotine chewing gum and the impractical aspects attendant intravenous or subcutaneous injection of nicotine. It was also pointed out that an elevated nicotine level could be maintained during hours of sleeping to reduce the initial early morning cigarette craving due to low nicotine levels in the body.

There are many applications of transdermal drug delivery devices (TDDD's) in the medical area in which patients require 24-hour medication regimens, exhibit impaired liver function and/or display gastrointestinal irritation to certain medicinal agents (MA's). Additionally, TDDD's are useful in the administration of MA's exhibiting narrow therapeutic ranges and/or short biologial half-lifes. As alluded to above, TDDD's currently available are of the following three types: (1) reservoir type in which pure or suspended MA is retained behind a semi-permeable membrane, which membrane is in contact with the skin; (2) monolith type in which pure or suspended MA is dispersed in a membrane, which membrane is in contact with the skin; and (3) adhesive dispersion type in which pure or suspended MA is dispersed in the adhesive layer of the TDDD, which layer is in contact with the skin. Although numerous modifications of these three types exist in the literature and in patents filed worldwide, these modifications exert only minimal effects on release kinetics.

In a variant of the present invention, the MA is included in any of the three prior art types of TDDD's described above in a microencapsulated, inactive or latent form exhibiting escape tendency and vapor pressure values that approach zero.

Alternatively, a more complex system containing the species with the general formulation MA-X and D-Y are included in the TDDD in separate microencapsulated forms; one or both forms may be microencapsulated but one must be microencapsulated. (MA=Medicinal Agent; X=Counter Ion; D=Displacing Species, i.e. displaces MA from X; Y=Counter Ion of D).

These TDDD's containing microencapsulated species offer distinct advantages over the existing TDDD's. These are as follows: (1) increased stability of oxygen labile MA's; (2) increased accuracy of initial MA dosage adminsitraton; and (3) flexibility in rate of MA dosage administration, i.e. only part of the microencapsulated species need be activated initially, leaving the remainder for subsequent (sequential) activation(s). In order to activate the TDDD, the patient applies the device to the skin then physically disrupts the microencapsulation by pressing the exterior side of the TDDD. The result is a rise in MA escape tendency and vapor pressure with a concomitant release of MA from the TDDD at a desirable kinetic rate that circumvents the burst effect.

Although the present invention was primarily developed as a vehicle for absorption of nicotine to assist in compliance with smoking cessation programs, it is apparent that other drugs could be equally well administered. And, the rate of administration without the abrupt change in delivery levels attendant prior art devices would be obviated.

While the principles of the invention have now been made clear in an illustrative embodiment, there will be immediately obvious to those skilled in the art many modifiations of structure, arrangement, proportions, elements, materials, and components, used in the practice of the invention which are particularly adapted for specific environments and operating requirements without departing from those principles.

I claim:

1. A transdermal drug delivery device, said device comprising in combination:
   (a) a plurality of interlaminar layers for adsorbing the drug to be delivered;
   (b) a plurality of adhesive laminae for containing the drug to be delivered interspersed in stacked relationship with said plurality of interlaminar layers, said plurality of adhesive laminae being permeated with the drug to be delivered;
   (c) a layer of contact adhesive for securing the stack of said plurality of interlaminar layers and said plurality of adhesive laminae to a user's skin; and
   (d) an impermeable covering disposed at least proximate the stack of said plurality of interlaminar layers and said plurality of adhesive laminae for preventing dispersion of the drug to be delivered.

2. The device as set forth in claim 1 wherein each interlaminar layer of said plurality of interlaminar layers includes particulates for adsorbing the drug to be delivered.

3. The device as set forth in claim 1 wherein each interlaminar layer of said plurality of interlaminar layers includes at least a monolayer of drug adsorbing particulates.

4. The device as set forth in claim 3 wherein each interlaminar layer of said plurality of interlaminar layers includes at least a bilayer of drug adsorbing particulates.

5. The device as set forth in claim 1 including a liner extending across the stack of said plurality of interlaminar layers and said plurality of adhesive laminae for preventing dispersion of the drug prior to use.

6. The device as set forth in claim 5 wherein said covering extends along the sides of the stack of said plurality of interlaminar layers and said plurality of adhesive laminae.

7. The device as set forth in claim 1 wherein the drug is nicotine.

8. A transdermal drug delivery device, said device comprising in combination:
   (a) a stack of layers for adsorbing the drug to be delivered interspersed with laminae for containing the drug to be delivered;
   (b) a drug transmittable adhesive for securing one end of said stack to a user's skin;
   (c) a covering for discouraging dispersal of the drug from said stack; and
   (d) a removable liner for discouraging dispersal of the drug from said stack prior to use.

9. The device as set forth in claim 8 wherein said covering extends along the sides of said stack.

10. The device as set forth in claim 9 wherein said covering is secured with said liner prior to removal of said liner.

11. A method for transdermally delivering a drug, said method comprising the steps of:
    (a) adsorbing the drug to be delivered in a plurality of interlaminar layers;
    (b) containing the drug to be delivered in a plurality of adhesive laminae interspersed in stacked relationship with the plurality of interlaminar layers;
    (c) securing one end of the stack of interspersed interlaminar layers and adhesive laminae to a user's skin; and
    (d) preventing dispersion of the drug to be delivered from the stack.

12. The method as set forth in claim 11 including the step of preventing dispersion of the drug from the stack prior to exercise of said step of securing.

13. The method as set forth in claim 11 wherein said step of containing includes the step of migrating molecules of the drug through the stack of interspersed interlaminar layers and adhesive laminae upon transdermal delivery of the drug.

14. The method as set forth in claim 13 wherein said step of migrating includes the step of delivering the drug transdermally at an essentially constant, but declining, rate.

15. The method as set forth in claim 14 including the step of exercising said step of delivering for at least eight hours.

16. The method as set forth in claim 11 including the step of delivering the drug transdermally with an initial burst effect.

17. The method as set forth in claim 16 including the step of delivering the drug transdermally at an essentially constant, but declining, rate after the initial burst delivery of the drug.

18. The method as set forth in claim 11 wherein the drug delivered is nicotine.

19. A method for transdermally delivering a drug, said method comprising the steps of:
(a) containing the drug to be delivered in each lamina of a plurality of laminae;
(b) interspersing in a stacked relationship the plurality of laminae with a plurality of layers;
(c) dispersing the drug transdermally from one end of the stack of interleaved laminae and layers; and
(d) migrating the drug from the laminae through the layers to the point of drug dispersal during said step of dispersing.

20. The method as set forth in claim 19 wherein the drug transdermally disbursed is nicotine.

21. The method as set forth in claim 19 wherein said step of dispersing includes the step of dispersing the drug at an essentially constant, but declining, rate.

22. The method as set forth in claim 21 wherein said step of dispersing is carried out for at least eight hours.

23. The method as set forth in claim 19 wherein said step of dispersing is carried out with an initial burst effect.

24. The method as set forth in claim 23 wherein said step of dispersing is carried out at an essentially constant, but declining, rate after the initial delivery burst.

25. A method for delivering a drug transdermally for an extended period of time, said method including the steps of:
(a) containing the drug to be delivered in each lamina of a plurality of stacked laminae;
(b) migrating molecules of the drug from one lamina to another lamina in a cascade manner through the stacked laminae to one end of the stacked laminae which one end is at the location of transdermal delivery; and
(c) preventing dispersion of the drug from the other end of the stacked lamina.

26. The method as set forth in claim 25 wherein said step of migrating includes the step of adsorbing the drug in layers interspersed with the stacked laminae.

27. The method as set forth in claim 26 including the step of prventing dispersion of the drug from the one end of stacked lamina prior to exercise of said step of migrating.

28. The method as set forth in claim 27 including the step of adhering the stacked lamina to the skin of a user after cessation exercise of said step of preventing.

29. The method as set forth in claim 25 including the step of housing the drug to be delivered in at least one well type reservoir.

30. The method as set forth in claim 29 including the step of maintaining the drug to be delivered within each well type reservoir with a fracturable cover.

31. The method as set forth in claim 30 including the step of fracturing the cover to provide for migration of the drug from the well type reservoir to the transdermal delivery location.

32. The method as set forth in claim 29 wherein said step of housing includes housing a plurality of friable microcapsules encapsulating the drug to be delivered in at least one well.

33. The method as set forth in claim 32 including the step of rupturing at least some of the microcapsules to provide for migration of the drug from the well type reservoir to the transdermal delivery location.

34. A method for delivering a drug transdermally for an extended period of time, said method including the steps of:
(a) housing the drug to be delivered in a well type reservoir;
(b) migrating molecules of the drug through one lamina to another lamina in a cascade manner through a stack of laminae to one end of the stacked laminae which one end is at the location of transdermal delivery; and
(c) preventing dispersion of the drug from the other end of the stacked laminae.

35. The method as set forth in claim 34 including the step of maintaining the drug to be delivered within the well type reservoir with a fracturable cover.

36. The method as set forth in claim 35 including the step of fracturing the cover to provide for migration of the drug from the well type reservoir to the transdermal delivery location.

37. The method as set forth in claim 34 wherein said step of housing includes housing a plurality of friable microcapsules encapsulating the drug to be delivered in at least one well type reservoir.

38. The method as set forth in claim 37 including the step of rupturing at lease some of the microcapsules to provide for migration of the drug from the well type reservoir to the transdermal delivery location.

39. A transdermal drug delivery device, said device comprising in combination:
(a) a well type reservoir for housing the drug to be delivered;
(b) at least one interlaminar layer for adsobing the drug to be delivered;
(c) at least one adhesive lamina for receiving the drug to be delivered, each said adhesive lamina being in interleaved stacked relationship with each of said interlaminar layers, said well type reservoir forming a part of the stack;
(d) a layer of contact adhesive for securing one end of the stack comprising said well, said adhesive lamina and said interlaminar layer to a user's skin; and
(e) an impermeable covering disposed at least proximate the other end of the stack for preventing dispersion therefrom of the drug to be delivered.

40. The device as set forth in claim 39 wherein said well type reservoir includes a plurality of friable microcapsules encapsulating the drug to be delivered.

41. The device as set forth in claim 39 including a fracturable cover for retaining the drug in said well type reservoir prior to fracturing said cover.

42. The device as set forth in claim 39 including a plurality of said well type reservoirs.

43. The device as set forth in claim 42 wherein each of said plurality of well type reservoirs comprise a part of the stack.

44. The device as set forth in claim 43 including means for selectively accommodating outflow of the drug from each of said plurality of well type reservoirs.

* * * * *